United States Patent
Pacetti et al.

(12)

(10) Patent No.: US 6,355,058 B1
(45) Date of Patent: Mar. 12, 2002

(54) STENT WITH RADIOPAQUE COATING CONSISTING OF PARTICLES IN A BINDER

(75) Inventors: Stephen Pacetti, San Jose; Joanna Mroz, Mountain View, both of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/475,378

(22) Filed: Dec. 30, 1999

(51) Int. Cl.$^7$ .................................................. A61F 2/06
(52) U.S. Cl. ...................... 623/1.15; 623/1.34; 427/2.25
(58) Field of Search ............................. 623/1.34, 1.46; 606/194; 528/361; 427/2.1–2.31

(56) References Cited

U.S. PATENT DOCUMENTS

| | | |
|---|---|---|
| 3,105,492 A | 10/1963 | Jeckel |
| 3,657,744 A | 4/1972 | Ersek |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haerr |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |

(List continued on next page.)

FOREIGN PATENT DOCUMENTS

| | | |
|---|---|---|
| EP | 0045627 | 2/1982 |
| EP | 0062300 A2 | 10/1982 |
| EP | 0221570 A2 | 5/1987 |
| EP | 0335341 B1 | 10/1989 |
| EP | 0338816 A2 | 10/1989 |
| EP | 0357003 A2 | 3/1990 |
| EP | 0361192 A3 | 4/1990 |
| EP | 0364787 A1 | 4/1990 |
| EP | 0372789 A3 | 6/1990 |
| EP | 0380668 B1 | 8/1990 |

(List continued on next page.)

OTHER PUBLICATIONS

Charnsangavej, Chuslip, M.D., et al., Stenosis of the Vena Cava: Preliminary Assessment of Treatment With Expandable Metallic Stents, *Radiology*, pp. 295–298, vol. 161, Nov. 1986.*

Rösch, Josef, M.D., et al., Experimental Intrahepatic Portacaval Anastomosis: Use of Expandable Gianturco Stents, *Radiology*, pp. 481–485, vol. 162, No. 1987.*

Rösch, Josef, M.D., et al., Modified Gianturco Expandable Wire Stents in Experimental and Clinical Use, *Annales de Radiologie*, pp. 100–103, vol. 31, No. 2, 1998.*

Lawrence, David D., Jr., et al., Percutaneous Endovascular Graft: Experimental Evaluation, *Radiology* pp. 357–360, vol. 163, May 1987.*

Rösch, Josef, et al., Gianturco Expandable Stents in Experimental and Clinical Use, pp. 121–124, Twelfth Annual Course on "Diagnostic Angiography and Interventional Radiology" Mar. 23–26, 1987, San Diego, California.*

(List continued on next page.)

*Primary Examiner*—David H. Willse
*Assistant Examiner*—Suzette J. Jackson
(74) *Attorney, Agent, or Firm*—Fulwider Patton Lee & Utecht, LLP

(57) ABSTRACT

A stent configuration wherein particles of radiopaque material contained within a polymeric binder is coated onto a stent core structure to enhance the radiopacity of the stent. The stent is initially formed and rendered radiopaque after all surfaces are coated with the radiopaque coating. The amount of particles of radiopaque materials can be varied (by volume) within the binder to either increase or decrease the radiopacity of the binder coating in order to obtain an optimal amount of radiopacity to the stent. The thickness of the coating also can be varied to fine tune the radiopacity of the stent.

26 Claims, 1 Drawing Sheet

U.S. PATENT DOCUMENTS

| | | |
|---|---|---|
| 4,531,933 A | 7/1985 | Norton et al. |
| 4,553,545 A | 11/1985 | Maass et al. |
| 4,580,568 A | 4/1986 | Gianturco |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,681,110 A | 7/1987 | Wiktor |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,762,128 A | 8/1988 | Rosenbluth |
| 4,767,418 A | 8/1988 | Deininger et al. |
| 4,776,337 A | 10/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,922,905 A | 5/1990 | Strecker |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,195,984 A | 3/1993 | Schatz |
| 5,197,978 A | 3/1993 | Hess |
| 5,206,341 A * | 4/1993 | Ibay et al. .................. 528/361 |
| 5,222,971 A | 6/1993 | Willard et al. |
| 5,226,913 A | 7/1993 | Pinchuk |
| 5,234,456 A | 8/1993 | Silvestrini |
| 5,242,452 A | 9/1993 | Inoue |
| 5,282,823 A | 2/1994 | Schwartz et al. |
| 5,282,824 A | 2/1994 | Gianturco |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,356,433 A | 10/1994 | Rowland et al. |
| 5,415,546 A * | 5/1995 | Cox, Sr. .................. 433/202.1 |
| 5,423,885 A | 6/1995 | Williams |
| 5,617,878 A | 4/1997 | Taheri |
| 5,639,278 A * | 6/1997 | Dereume et al. .......... 623/1.15 |
| 5,843,118 A * | 12/1998 | Sepetka et al. ............. 606/194 |
| 5,938,697 A | 8/1999 | Killion et al. |
| 6,174,330 B1 * | 1/2001 | Stinson ...................... 623/1.34 |
| 6,019,789 A1 * | 2/2001 | Dinh et al. ................. 623/1.35 |
| 6,184,266 B1 * | 2/2001 | Ronan et al. ............... 523/113 |

FOREIGN PATENT DOCUMENTS

| | | |
|---|---|---|
| EP | 0407951 A2 | 1/1991 |
| EP | 0421729 A2 | 4/1991 |
| EP | 0423916 A1 | 4/1991 |
| EP | 0428479 B1 | 5/1991 |
| EP | 0517075 B1 | 12/1992 |
| EP | 0540290 B1 | 5/1993 |
| EP | 0541443 A1 | 5/1993 |
| FR | 2677872 | 12/1992 |
| GB | 2070490 A | 9/1981 |
| GB | 2135585 A | 9/1984 |
| JP | 58-501458 | 9/1983 |
| JP | 62 231657 | 10/1987 |
| JP | 62235496 A | 10/1987 |
| JP | SHO63-214264 | 9/1988 |
| JP | 01083685 A | 3/1989 |
| JP | 1-299550 | 12/1989 |
| JP | HEI02-174859 | 7/1990 |
| JP | HEI02-255157 | 10/1990 |
| JP | 3-9745 | 1/1991 |
| JP | 03009746 A | 1/1991 |
| JP | 3-151983 | 6/1991 |
| JP | HEI04-25755 | 2/1992 |
| WO | WO91/07139 | 5/1991 |
| WO | WO92/06734 | 4/1992 |
| WO | WO92/09246 | 6/1992 |
| WO | WO97/25937 | 7/1997 |
| WO | WO98/20927 | 5/1998 |
| WO | WO98/32412 | 7/1998 |
| WO | WO99/17680 | 4/1999 |
| WO | WO99/39661 | 8/1999 |

OTHER PUBLICATIONS

Dotter, Charles T., Transluminally Placed Coilspring Endarterial Tube Grafts, *Investigative Radiology*, pp. 329–332, Sep./Oct. 1969.

Rösh, J., M.D., et al., Transjugular Intrahepatic Portacaval Shunt: An Experimental Work, *The American Journal of Surgery*, pp. 588–592, vol. 121, May 1971.

Dotter, Charles T., Transluminal Expandable Nitinol Coil Stent Grafting: Preliminary Report, *Radiology Journal*, pp. 259–260, Apr. 1983.

Cragg, et al., Non–Surgical Placement of Arterial Endoprostheses: A New Technique Using Nitinol Wire, *Radiology Journal*, pp. 261–263, Apr. 1983.

Maas, et al., Radiological Follow–Up of Transluminally Inserted Vascular Endoprostheses: An Experimental Study Using Expanding Spirals, *Radiology Journal*, pp. 659–663, 1984.

$70^{th}$ Scientific Assembly and Annual Meeting: Scientific Program, *Radiology*, Washington, DC: Nov. 25–30, 1084, Special Edition, vol. 153(P).

C. R. Bard, Pe Plus Peripheral Balloon Dilatation Catheter, *C. R. Bard*, Inc., Aug. 1985.

Wright, et al., Percutaneous Endovascular Stents: An Experimental Evaluation, *Radiology Journal*, pp. 69–72, 1985.

Plamaz, et al., Expandable Intraluminal Graft; A Preliminary Study, *Radiology Journal*, pp. 73–77, 1985.

Program: Day 2 (Nov. 18) the Radiological Society of North American, *Radiology*, 1985.

Charnsangavej, C., M.D., et al., Endovascular Stent For Use In Aortic Dissection: An In Vitro Experiment, *Radiology*, pp. 323–324, vol. 157, No. 2, Nov. 1985.*

Wallace, Michael J., et al., Tracheobronchial Tree: Expandable Metallic Stents Used In Experimental And Clinical Applications (Work In Progress), *Radiology*, pp. 309–312, vol. 158, Feb. 1986.*

$72^{nd}$ Scientific Assembly And Annual Meeting: RSNA Scientific Program, *Radiology*, Chicago: Nov. 30–Dec. 5, 1986, Special Edition vol. 161(P).*

Duprat, et al., Flexible Balloon–Expanded Stent For Small Vessels, *Radiology Journal*, pp. 276–278, 1987.*

Rösch, Josef, M.D., et al., Gianturco Expandable Stents In Experimental And Clinical Use, paper presented at The Twelfth Annual Course on "Diagnostic Angiography and Interventional Radiology" Mar. 23–26, 1987 (San Diego, California).*

Rösch, Joseph, M.D., et al., Gianturco Expandable Wire Stents In The Treatment Of Superior Vena Cava Syndrome Recurring After Maximum–Tolerance Radiation, *Cancer*, pp. 1243–1246, vol. 60, Sep. 1987.

Yoshioka, Tetsuya, et a., Self–Expanding Endovascular Graft: An Experimental Study In Dogs, *American Journal of Roentgeriology*, pp. 673–676, vol. 151, Oct. 1988.

Yoshioka, et al., Development And Clinical Application Of Biliary Endoprostheses Using Expandable Metallic Stents, *Japan Radiological Society*, 1988, vol. 48, No. 9, pp. 1183–1185 (with translation).

Mirich, et al., "Percutaneously Placed Endovascular Grafts For Aortic Aneurysms: Feasibility Study", *Radiology*, 1989, Part 2, pp. 1033–1037.

* cited by examiner

STENT WITH RADIOPAQUE COATING CONSISTING OF PARTICLES IN A BINDER

BACKGROUND OF THE INVENTION

The present invention generally relates to endoprosthesis devices, most often referred to as stents, and more particularly pertains to increasing the radiopacity of such devices.

Stents or expandable grafts are implanted in a variety of body lumens in an effort to maintain their patency and are especially well-suited for the treatment of atherosclerotic stenosis in blood vessels. Intercoronary stents have become a standard adjunct to percutaneous coronary angioplasty in the treatment of arterial atherosclerotic disease. Although commercial stents vary in design and materials, they share similar structural features. Most current stents in clinical use are metallic and are either self-expanding or are expanded by the force of an expandable member, such as an angioplasty dilatation balloon. These devices are typically implanted via a delivery catheter which is inserted at an easily accessible location on the patient and then advanced through the patient's vasculature to the deployment site. The stent is initially maintained in a radially compressed or collapsed state to enable it to be maneuvered through the lumen and into the stenosis. Once in position, the stent is deployed which, depending upon its construction, is achieved either automatically by the removal of a restraint, or actively by the inflation of a balloon about which the stent is carried on the delivery catheter.

The stent must be able to simultaneously satisfy a number of mechanical requirements. First and foremost, the stent must be capable of withstanding the structural loads that are imposed thereon as it supports the lumen walls. In addition to having adequate radial strength or more accurately, hoop strength, the stent should nonetheless be longitudinally flexible to allow it to be maneuvered through a tortuous vascular path and to enable it to conform to a deployment site that may not be linear or may be subject to flexure. The material of which the stent is constructed must allow the stent to undergo expansion which typically requires substantial deformation of localized portions of the stent's structure. Once expanded, the stent must maintain its size and shape throughout its service life despite the various forces that may come to bear upon it, including the cyclic loading induced by the pulsatile character of arterial blood flow. Finally, the stent must be biocompatible so as not to trigger any adverse vascular responses.

Fluoroscopy has typically been relied upon to facilitate the precise placement of a stent as well as to verify the position of a stent within a patient throughout its service life. The use of radiopaque materials in the construction of the stent allows for its direct visualization. Unfortunately, no single material to date has been identified that simultaneously satisfies all requirements inherent in a stent application. Those materials that do satisfy the mechanical requirements are either insufficiently or excessively radiopaque and/or have not been adequately proven to be biocompatible in a vascular setting. Thus, with current stent materials, constructing a radiopaque stent wholly out of a single material has not provided an optimal solution. A number of different approaches, however, have been employed wherein different materials are combined in an effort to render a mechanically sound and biocompatible stent to be visible by a fluoroscope system.

Several metals, such as stainless steel, nickel titanium alloys, tantalum and platinum alloys have been used to construct stents. These materials vary widely in their mechanical properties and radiopacity. All these materials can, by varying the design, be used to create the sent. However, the mechanical and radiopacity characteristics are not independent, but linked. Strength requirements dictate, for example, the strut thickness, geometry and percentage of the arterial wall which is to be covered by the stent structure. The resulting radiopacity is largely fixed and can only be adjusted with an alteration of the mechanical characteristics of the stent. For some materials, such as tantalum, the resulting stents can be too radiopaque, which results in obscured images of the anatomy in the stent lumen. This makes, for example, visualization of any possible restenosis within the stent very difficult to visualize on a fluoroscope. Other stent designs comprising of less radiopaque materials, such as stainless steel or nitinol, can have excellent mechanical functionability, but offer sub-optimal radiopacity except in cases where the stent struts can be very thick, as in an aortic stent-graft. In addition, the short-term hemocompatability and long term biocompatability of stents could be improved. In a short time-frame, the issue of stent thrombogenicity may be critical since modern coronary stents have a low, but measurable, rate of short term (one to seven days) thrombotic occlusion. This is true even if the patient is provided with systemic anticoagulation therapy. Metals such as tantalum and stainless steel, although inert, are actually coated with serum proteins and, to the extent that they are still activated, platelets after insertion into the bloodstream. In long-term implantation, stents become endothelialized. Therefore, biocompatability, particularly the foreign body response, can be of great concern. Growth of smooth muscle cells with extra cellular matrix production may lead to the restenotic closing of the arterial lumen. Platelet derived growth factor from thrombus-bound platelets can stimulate smooth cell muscle cells to proliferate. Metal ions that leech from the stent may catalytically oxidized low density lipo-proteins which exacerbate the original atherosclerotic condition.

One means frequently described for accomplishing fluoroscopic visibility is the physical attachment of radiopaque markers to the stent. Conventional radiopaque markers, however, have a number of limitations. Upon attachment to a stent, such markers may project from the surface of the stent, thereby comprising a departure from the ideal profile of the stent. Depending on their specific location, the marker may either project inwardly to disrupt blood flow or outwardly to somewhat traumatize the walls of the blood vessel. Additionally, galvanic corrosion that might result from the contact of two disparate metals, i.e., the metal used in the construction of the stent and the radiopaque metal of the marker could corrode, and in the worst case, cause the marker to become separated from the stent which could be problematic should the marker be swept downstream. Although such markers are typically fairly small, this approach does cause the radiopaque material to come into direct contact with living tissue which may be problematic should there be any biocompatibility issues. Finally, markers also give an incomplete picture of the stent expansion and orientation. Usually there are two markers, one at each end. By making the entire stent radiopaque and visible, its degree of expansion and curvature for its full length can be assessed.

Stents also have been previously marked by coating selected portions thereof with radiopaque material. Radiopaque metals, such as gold, platinum and tantalum can be coated by sputtering, evaporation or electroplating processes. It is important that these coated layers have good adhesion and conform to the stent during deformation. The deformation is typically greatest during stent expansion. However, a number of disadvantages are associated with this approach as well. This again causes the radiopaque material to come into direct contact with living tissue which, depending on the total area that is coated, can amount to a sizeable exposure. Unfortunately, cracking, flaking and delamination can be a problem with this approach. When the stent is expanded and certain portions thereof are caused to undergo substantial deformation, there is a risk that cracks would form in the plating and that sections thereof would become separated from the underlying substrate. This has the potential for causing turbulence in the blood flowing thereover to thereby induce thrombogenesis. Depending on the size and number of particles, pieces will create an embolized hazard for downstream vasculature. Moreover, once the underlying structural material becomes exposed, interfaces between the two, disparate metals become subject to galvanic corrosion. Further, should the coating pattern cover less than all of the stent's surfaces, the margins between the coating and un-coated regions are subject to galvanic corrosion.

As a further alternative, a stent structure has been described that is formed from a sandwich of structural and radiopaque materials. Three tubes of the materials are codrawn and heat treated to create a structural/radiopaque/structural materials sandwich. Struts and spines (also known as "links") are then formed in the tube by cutting an appropriate pattern of voids (also known as "cells") into the tube as is well known in the art. While this approach does provide a stent that is radiopaque and that fulfills the necessary mechanical requirements, the thin cross section of the radiopaque material is nonetheless exposed along the edges of all cut lines. The biocompatibility of the radiopaque material therefore remains an issue and more significantly, a sizeable area may be created that is subject to galvanic corrosion. Any cuts in the sandwich structure cause two disparate metal interfaces, i.e., the juncture between the outer structural layer and the central radiopaque layer as well the juncture between the central radiopaque layer and the inner structural layer, to become exposed along the entire lengths of such cuts.

A stent configuration is therefore required that overcomes the shortcomings inherent in previously known devices. More specifically, a stent structure is needed that provides the requisite mechanical properties for such application, that exposes only fully biocompatible materials to living tissue and that is fluoroscopically visible.

SUMMARY OF THE INVENTION

The present invention provides a stent that overcomes the shortcomings of previously known stent devices. The stent fulfills all the mechanical and structural requirements attendant to its function as a stent. Moreover, the stent is fluoroscopically visible without any radiopaque material being exposed to living tissue and without any disparate metal interfaces being subject to galvanic corrosion.

The advantages of the present invention are achieved with the complete encapsulation of radiopaque particles within a binder that is dispersed onto the stent. In one embodiment, a substantially conventional stent is first formed of a structural material by any one of a number of conventional methods. The design should provide sufficient mechanical strength. Radiopaque particles are then placed in a binder which has satisfactory bio- and hemo-compatibility. The binder will then be coated on all surfaces of the stent in such a manner to produce a smooth surface. The thickness and particle loading of the radiopaque material can be adjusted to fine tune the degree of radiopacity needed, depending upon the choice of material used to create the stent. The radiopaque coating/binder may be applied by spraying, dipping, brushing, wiping, pad printing, electrostatic liquid spraying or electrostatic powder coating. Alternatively, therapeutic agents may also be included in the radiopaque coating/binder to serve as a reservoir for controlled drug delivery.

Potential metallic materials for the structural layer of the stent would include, but are not limited to, stainless steels, nickel titanium alloys, cobalt chromium alloys, tantalum and platinum alloys. The thickness in the radial direction of the structural stent should be in the range of about 25–250 microns, preferably in the range of 50–125 microns. Radiopaque materials which are suitable for use are generally materials of high atomic number, located in the bottom two rows coincident with the bottom two rows of the transition metal block of the periodic table. These materials may consist of iodine and its salts, barium and its salts or compounds, tantalum, tungsten, rhenium, osmium, iridium, noble metals, palladium, platinum, gold, colloidal gold, silver and bismuth and its salts or compounds. Oxides and compounds of the metals listed, such as iridium oxide, may also be used. A radiopaque coating/binder thickness should be in the range of about 0.1 to 25 microns, preferably in the range of 1 to 10 microns. Large coating thicknesses may possibly alter the geometry of the stent.

Materials for the binder can be varied and may consist of synthetic polymers or biopolymers. The polymer may be either biostable or bioresorbable. In the case where the polymer is bioresorbable, the radiopaque filler is released. Consequently, a bioresorbable filler such as an iodine salt would be used.

The stent configuration could be used in coronary, carotid, neurological, saphenous vein graph, venous, renal, iliac, biliary, or other peripheral stent designs. The stent may be self-expanding or expandable upon application of an external force, such as the expansion by a dilatation balloon.

These and other features and advantages of the present invention will become apparent from the following detailed description of preferred embodiments which, taken in conjunction with the accompanying drawings, illustrate by way of example the principles of the invention.

DETAILED DESCRIPTION OF THE PREFERRED EMBODIMENTS

A stent constructed in accordance with the present invention is employed to maintain the patency of selected body lumens in the conventional manner both in terms of application as well as deployment. The advantages afforded by the stent are inherent in its ability to provide the required strength, to provide the needed amount of radiopacity to ensure adequate visualization under a fluoroscope, to expose only biocompatible materials to living tissue, and to reduce the possibility of galvanic corrosion despite the fact that disparate metals are employed in its construction.

Figure 1:
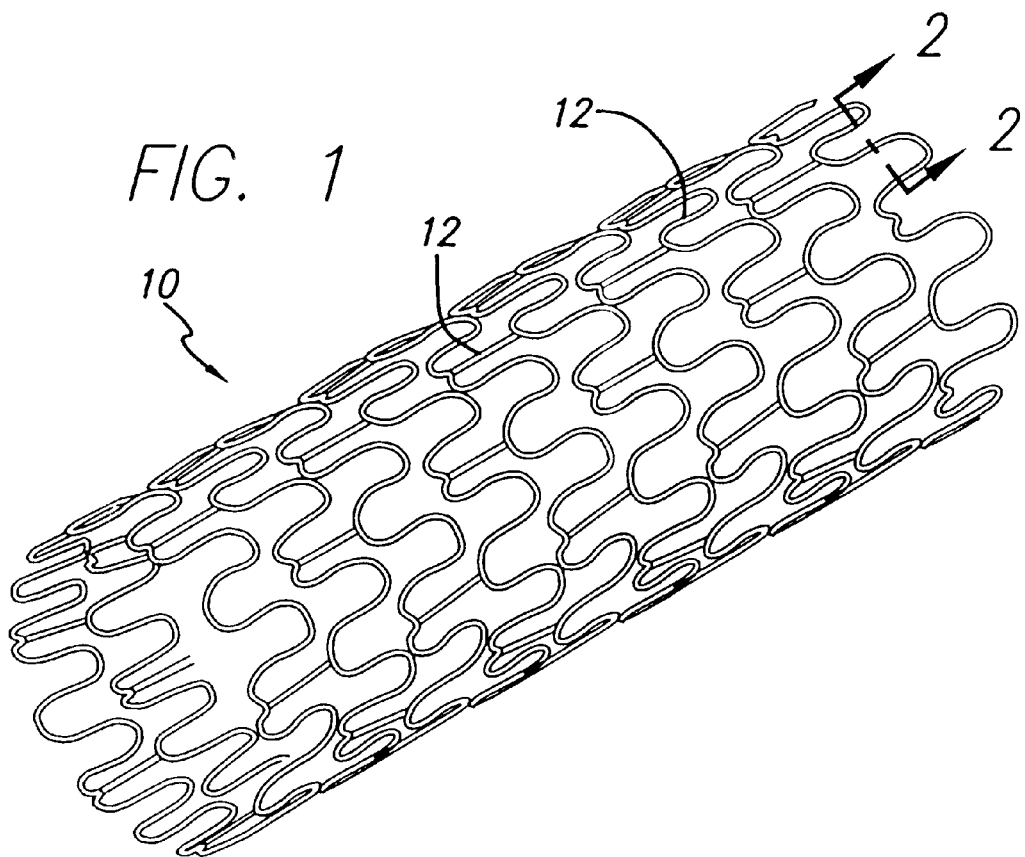
FIG. 1 is a perspective view of a stent of the present invention.

FIG. 1 illustrates a tubular stent 10 constructed in accordance with the present invention. The underlying structure can be formed in one preferred conventional manner wherein a tube has a carefully preselected pattern removed therefrom, such as by laser cutting, etching, micro-machining or electrical discharge metal removal, to achieve a desired strut pattern. The pattern of voids serves to define an intricate network of struts 12 to enable the tube to expand radially when subjected to appropriate radially directed forces, such as those exerted by the inflation of a dilatation balloon. A myriad of strut and spine patterns are known for achieving various design goals, such as enhancing strength, maximizing the expansion ratio, or coverage area, enhancing longitudinal flexibility or longitudinal uniformity upon expansion, and the like. One pattern may be selected over another in an effort to optimize those parameters that are of particular importance for a certain application.

Figure 2:
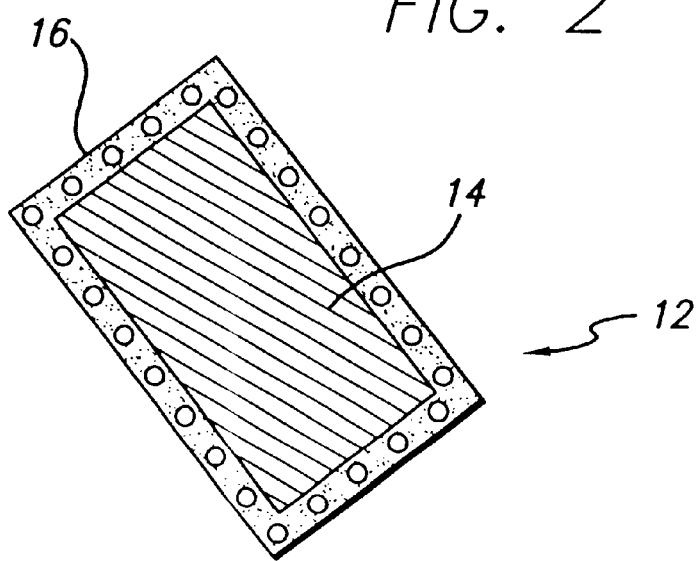
FIG. 2 is a greatly enlarged cross-sectional view taken along lines 2—2 of FIG. 1 illustrating one preferred embodiment of the present invention.

FIG. 2 is a cross-sectional view of the stent of the present invention and more specifically, is the cross-section of a single strut 12. Visible in the illustration are a total of two elements which include a central core 14 and an radiopaque coating 16. The central core 14 in fact comprises the underlying structure of the stent that is formed in the manner described above and defines the overall configuration of the stent. The material employed for such underlying structure is selected for its structural and mechanical properties and may be the same material of which conventional stents are exclusively formed. Suitable materials include, but are not limited to nickel-titanium, cobalt-based alloys, Nitinol, tantalum, platinum alloys and stainless steel. Stainless steel and more specifically stainless steel 316L alloy may be used.

The material used in the radiopaque coating 16 is selected for its radiopacity. This binder coating 16 consists of a binder and particles of radiopaque materials. Appropriate radiopaque materials include, but are not limited to iodine and its salts or compounds, barium and its salts or compounds, tungsten, rhenium osmium, noble metals, palladium, gold, colloidal gold, silver, platinum, tantalum, iridium or their alloys. Such materials are highly visible by fluoroscopy and are therefore visible even at very minimal thicknesses. A combination of issues involving mechanical properties, more specifically their low strength and high malleability and biocompatibility, preclude their exclusive use in the construction of a stent. Moreover, if such materials were to be used in sufficient thicknesses to afford the requisite strengths, they would typically appear so bright on the fluoroscope so as to obscure the stent deployment site and preclude visualization of features in the stent lumen. Accurate positioning of the stent, and more importantly, assessment of subsequent restenosis inside the stent, would therefore be rendered difficult. Finally, although many of the above listed radiopaque materials have been used in the human body for some time, their long-term effect in a vascular setting with tissue contact may or may not have been established.

Materials for the binder can be a variety of materials provided they satisfy the requirements for bio- and hemo-compatibility. They may consist of synthetic polymers or biopolymers. The polymer may be either biostable or bioresorbable. In instances where a bioresorbable polymer is used, the radiopaque particles would be released. This would create biocompatible issues unless the radiopaque particles were, for example, made of select barium, bismuth or iodine compounds. Specific examples for the synthetic polymer would include polytetrafluoroethylene, fluorinated ethylene-propylene, polyvinylidene fluoride, silicone, polyether urethanes, polycarbonate urethanes, urethanes containing surface modifying additives where these additives provide silicone, hydrocarbon, polyethylene glycol, or perfluorocarbon chains on the surface, polyurethanes with surface modifying endgroups consisting of silicone, hydrocarbon, polyethylene glycol or perfluoropolymer chains, olefinic polymers such as polyethylene and polypropylene, ethylene polymers such as ethylene vinyl acetate, ethylene coacrylic acid and ethylene covinyl alcohol, along with polyimide, polyethererketone, polyaryletherketone and polysulfone. Biodegradable polymers would include L-polylactide, polylactic acid, polyglycolic acid, copolymers of lactic and glycolic acid, polycaprolactone, polyanhydrides, polyphosphoesters, polyphosphazenes, polyhydroxyvalerate and polyhydroxybutyrate. Biopolymers would include fibrin, hyaluronic acid, chondroitin sulfate, heparin sulfate, heparin sulfate with hydrophobic counterions, heparin sulfate covalently bonded to the underlying surface, albumin, elastin, gelatin, and collagen. The radiopaque coating may be applied by spraying, dipping, brushing, wiping, pad printing, electrostatic liquid spraying, or electrostatic powder coating. Therapeutic agents may be included in the radiopaque coating to serve as a reservoir for controlled drug delivery.

The thickness in the radial direction of the structural material used for the central core 14 indicated above and the thickness of the structural layer in the radial direction would be in the range of about 25 to 250 microns, preferably in the range of 50 to 125 microns. The thickness of the radiopaque coating 16 would be in the range of about 0.1 to 25 microns, preferably in the range of 1 to 10 microns. The thickness of the coating can be varied to "fine tune" the desired radiopacity for the stent. Large coating thicknesses could possibly alter the geometry and mechanical properties of the stent. It is desirable to have a smooth surface for this outer radiopaque coating 16 to avoid possible formation of thrombosis once the stent is in place in the patient's vasculature. Hence, the size of the radiopaque particle should be much less than the coating thickness, and ideally less than one tenth the size of the coating thickness. For example, with a six micron coating, well-disbursed radiopaque particles in the range of about 0.6 microns can result in a smooth coating. For maximum radiopacity, the coating 16 must be loaded as much as possible. Coating flexibility and strength will diminish as the radiopaque particle loading increases. Geometry dictates a practical upper limit of about 66% particles by volume in a coating which is packed with closely packed spheres of radiopaque particles. A practical upper limit for particle loading is approximately 50% by volume.

The stent of the present invention can be formed by any of a number of well known methods such as laser cutting a pattern in a tube, chemical etching a pattern in tube, and electron discharge machining (EDM) a pattern in a tube. Each of these methods also can be used to form a stent pattern in a flat sheet which is then rolled into a cylinder and a longitudinal weld attaches the longitudinal edges of the stent. Such stent processes require electropolishing, which is well known, to remove processing impurities and form a smooth stent surface.

In manufacturing a stent as is illustrated in FIG. 1, and more particularly in FIG. 2, a tube of 316L stainless steel or other suitable material is first laser cut to provide a desired pattern of voids defining struts and spines, all in accordance with well known and well established procedures. After the voids have been cut into the tube, the surfaces of the cut tubing may be mechanically polished or electropolished to provide an extremely smooth surface. Electropolishing is a well known technique wherein the workpiece is immersed in an acidic solution and subjected to an electric potential. In the treatment of stainless steel, the procedure not only serves to smooth out the surface, but additionally serves to remove iron from near the surface to leave behind a chromium-rich stratum with enhanced corrosion resistance. The stent core preferably is subjected to the electropolishing step for a period of time sufficient to reduce the wall thickness of the stainless steel core to an acceptable predefined thickness. Alternatively, bead blasting or microsanding may be employed to achieve a sufficiently smooth surface.

The radiopaque coating 16 is subsequently applied to the electropolished central core 14. This radiopaque coating 16 may be applied by spraying, dipping, brushing, wiping, pad printing, electrostatic liquid spraying or electrostatic powder coating. Note that since the applied coating may smooth the surface further, the underlying stent may not need to be electropolished to as high a degree as a conventional stent. A surface primer or surface treatment may be applied to the metal stent surface before coating in order to optimize the adhesion of the coating. The radiopaque coating 16 may be applied to the entire stent structure or to only selected portions thereof through the use of masks. Advantageously selected patterns of radiopacity allow the precise orientation or degree of expansion to be discerned by inspection of the fluoroscopic image. The radiopaque coating 16 could utilize radiopaque materials which are permanent or, if one wanted temporary radiopacity, a coating could be formulated to provide only a short time increase in radiopacity. For example, coating can be formulated of biodegradable 1-polylactide containing barium or iodine salts. Such a coating would be radiopaque initially, but then would be absorbed within the body over a period of time. Future arterial visualization would be optimized since the remaining stent core would not obscure the lumen.

The stent configuration of the present invention could be used for coronary, carotid, neurological, saphenous vein graft, venous, renal, iliac, biliary, or other peripheral stent designs. The stents may be self-expanding or made to be balloon expandable. There is no inherent limitation on the stent's diameter or length, and as such will be dependent upon a particular application for the stent. Again, the manner and shape of the stents made in accordance with the present invention are numerous and can be made from a tubular segment or alternatively shaped with wire or wire-like meshing. The radiopaque coating 16 of the present invention can also be utilized on other prosthetic devices which require enhanced radiopacity to improve visualization under a fluoroscope.

While a particular form of the invention has been illustrated and described, it will also be apparent to those skilled in the art that various modifications can be made without departing from the spirit and scope of the invention. More specifically, it should be clear that the present invention is not limited to tubular type stents nor is it limited to any particular method of forming the underlying stent structure. Additionally, the invention is not limited to the use of any particular materials in the stent core, binder or radiopaque particles nor is it intended to be limited to any particular coating or application method. Accordingly, it is not intended that the invention be limited except by the appended claims.

What is claimed:

1. A radiopaque stent, comprising:
   a central core structure defining the shape of the stent; and
   a biocompatible outer radiopaque coating having particles of a radiopaque material dispersed within a binder which coats the central core structure, wherein the size of the particles of radiopaque material is no more than one tenth of the thickness of the coating.

2. The stent of claim 1, wherein said central core structure is made from a material selected from the group consisting of stainless steel alloys, cobalt chromium alloys, titanium alloys, and cobalt-chromium molybdenum alloys.

3. The stent of claim 1, wherein said central core structure is made from a nickel-titanium alloy.

4. The stent of claim 1, wherein said radiopaque particle material is formed from the group of materials consisting of gold, platinum, iridium, tantalum, silver, molybdenum, iodine and its salts or compounds, barium and its salts or compounds, bismuth and its salts or compounds, tungsten, rhenium, osmium, noble metals and palladium.

5. The stent of claim 1, wherein radiopaque coating has a thickness in the range of 0.1 to 25 microns.

6. The stent of claim 1, wherein the percentage of particles of radiopaque material within the binder is in the range of 10% to 66% by volume.

7. The stent of claim 1, wherein the percentage of particles of radiopaque material within the binder is approximately 15–40% by volume.

8. The stent of claim 1, wherein the binder is formed from the group of materials consisting of polymers and biopolymers.

9. The stent of claim 1, wherein the binder consists of a polymer which is biostable.

10. The stent of claim 1, wherein the binder is formed from the group of materials consisting of polytetrafluoroethylene, fluorinated ethylene-propylene, polyvinylidene fluoride, silicone, polyether urethanes, polycarbonate urethanes, urethanes containing surface modifying additives where these additives provide silicone, hydrocarbon, polyethylene glycol, or perfluorocarbon chains on the surface, polyurethanes with surface modifying endgroups consisting of silicone, hydrocarbon, polyethylene glycol or perfluoropolymer chains, olefinic polymers including polyethylene and polypropylene, ethylene polymers such as ethylene vinyl acetate and ethylene covinyl alcohol, and polymide, polyetheretherketone, polyaryletherketone and polysulfone.

11. The stent of claim 1, wherein the binder is formed from the group of materials consisting of L-polylactide, polylactic acid, polyglycolic acid, copolymers of lactic and glycolic acid, polycaprolactone, polyanhydrides, polyphosphoesters, polyphosphazenes, polyhydroxyvalerate, and polyhydroxybutyrate.

12. The stent of claim 1, wherein the binder is formed from the group of materials consisting of fibrin, elastin, hyaluronic acid, chondroitin sulfate, heparin sulfate, heparin sulfate with hydrophobic counterions, heparin covalently bonded to the underlying surface, albumin, gelatin, and collagen.

13. The stent of claim 1, wherein said radiopaque material is applied to all surfaces of the central core.

14. The stent of claim 1, wherein said radiopaque material is applied to less than all surfaces of the central core.

15. A method for forming a radiopaque stent, comprising the steps of:
   providing a tube of structural material;
   forming voids in said tube to render said tube expandable; and
   coating said expandable tube with a binder having particles of a radiopaque material, wherein the size of the particle of radiopaque material is no more than one-tenth of the thickness of the coating.

16. The method of claim 15, further comprising the step of electropolishing said expandable tube prior to said coating step.

17. The method of claim 15, wherein said voids are formed in said tube by laser cutting.

18. The method of claim 15, wherein the method of coating the expandable tube includes spraying, dipping, brushing, wiping, pad printing, elecrostatic liquid spraying, and electrostatic powder coating.

19. The method of claim 15, wherein said radiopaque coating is applied to all portions of said expandable tube.

20. The method of claim 15, wherein said radiopaque coating is applied to only selected portions of said expandable tube.

21. The method of claim 15, wherein the particles of radiopaque material are selected from the group consisting of iodine and its salts or compounds, barium and its salts or compounds, bismuth and its salts or compounds, tungsten, rhenium, osmium, noble metals, palladium, gold, colloidal gold, molybdenum, silver, platinum, tantalum, iridium and their alloys.

22. A radiopaque stent, comprising:
 a central core structure defining the shape of said stent; and
 a biocompatible outer radiopaque coating having particles of a radiopaque material dispersed within a binder which coats the central core structure, the particles being made from a material having temporary radiopacity.

23. The stent of claim 22, wherein said central core structure is made from a material selected from the group consisting of stainless steel alloys, cobalt chromium alloys, titanium alloys, and cobalt-chromium molybdenum alloys.

24. The stent of claim 22, wherein said central core structure is made from a nickel-titanium alloy.

25. The stent of claim 22, wherein the radiopaque material is formed from 1-polylactide containing barium or iodine salts.

26. The stent of claim 22, wherein radiopaque coating has a thickness in the range of 0.1 to 25 microns.

* * * * *

UNITED STATES PATENT AND TRADEMARK OFFICE
CERTIFICATE OF CORRECTION

PATENT NO. : 6,355,058 B1 Page 1 of 1
DATED : March 12, 2002
INVENTOR(S) : Stephen Pacetti and Joanna Mroz It is certified that error appears in the above-identified patent and that said Letters Patent is hereby corrected as shown below:

<u>Title page,</u>
U.S. PATENT DOCUMENTS, add
-- 5,607,442   3/1997         Fischell, et al,
5,702,682      12/1997        Thompson,
5,980,566      11/1999        Alt, et al. --.

FOREIGN PATENT DOCUMENTS, add
-- EP 0824900 A2    2/1998
EP 0916317 A1       5/1999
EP 0938879 A2       9/1999 --.

OTHER PUBLICATIONS, change "Plamaz", to -- Palmaz --.

Signed and Sealed this

Third Day of September, 2002

*Attest:*

*Attesting Officer*

JAMES E. ROGAN
*Director of the United States Patent and Trademark Office*